United States Patent [19]

Kohwi-Shigematsu et al.

[11] Patent Number: 5,624,799
[45] Date of Patent: Apr. 29, 1997

[54] CANCER-ASSOCIATED MAR BINDING PROTEIN

[75] Inventors: Terumi Kohwi-Shigematsu; Yoshinori Kohwi, both of San Diego, Calif.

[73] Assignee: The Burnham Institute, La Jolla, Calif.

[21] Appl. No.: 388,023

[22] Filed: Feb. 13, 1995

[51] Int. Cl.⁶ .......................... C12Q 1/68; G01N 33/574; G01N 33/566; G01N 33/48

[52] U.S. Cl. ................ 435/6; 435/7.23; 436/501; 436/64; 436/813; 530/358; 530/387.7

[58] Field of Search .................... 530/828, 850, 530/358, 387.7, 388.1, 388.15, 388.2, 389.1, 389.7; 435/6, 7.23

[56] References Cited

PUBLICATIONS

Dickinson, Liliane A. et al., "A Tissue-Specific MAR/SAR DNA-Binding Protein with Unusual Binding Site Recognition." *Cell* 70:631–645 (1992).

Nakagomi, K et al., "A Novel DNA-Binding Motif in the Nuclear Matrix Attachment DNA-Binding Protein SATB1." *Mole. Cell. Biol.* 14:1852–1860 (1994).

Dickinson, Liliane A. and Kohwi-Shigematsu, Terumi "Nucleolin is a Matrix Attachment Region DNA-Binding Protein That Specifically Recognizes a Region with High Base-Unpairing Potential." *Mole. Cell. Biol.* 15:456–465 (1995).

Fey, Edward G. and Penman, Sheldon "Nuclear Matrix Proteins Reflect Cell Type of Origin in Cultured Human Cells." *Proc. Natl. Acad. Sci. USA* 85:121–125 (1988).

Khanuja, Parvinderjit S. et al., "Nuclear Matrix Proteins in Normal and Breast Cancer Cells." *Cancer Res.* 53:3394–3398 (1993).

Luderus, M. E. Eva et al., "Binding of Matrix Attachment Regions to Lamin $B_1$." *Cell* 70:949–959 (1992).

von Kries, Jens P. et al., "Chicken MAR Binding Protein p120 is Identical to Human Heterogeneous Nuclear Ribonucleoprotein (hnRNP) U." *Nucleic Acids Res.* 22:1215–1220 (1994).

von Kries, Jens P. et al., "A Matrix/Scaffold Attachment Region Binding Protein: Identification, Purification, and Mode of Binding." *Cell* 64:123–135 (1991).

*Primary Examiner*—Toni R. Scheiner
*Assistant Examiner*—Yvonne Eyler
*Attorney, Agent, or Firm*—Campbell & Flores

[57] ABSTRACT

The present invention provides a substantially purified protein, p114-MBP, which has an apparent molecular mass of about 114 kDa and specifically associates with a matrix attachment region DNA sequence context (MAR). p114-MBP is characterized, in part, by having substantial MAR binding activity in malignant tumor tissue but not in a corresponding non-cancerous tissue. The invention also provides a method of detecting the presence of malignant tumor tissue in a cell sample suspected of containing malignant tumor tissue by contacting the sample with a MAR, under conditions that allow the specific association of the MAR with p114-MBP, and detecting such specific association, which indicates the presence of malignant tumor tissue in the cell sample. The present invention further provides a method of diagnosing cancer in a subject suspected of having cancer by contacting a cell sample obtained from a subject with a MAR under conditions that allow the specific association of the MAR with p114-MBP and detecting such specific association, which indicates that malignant tumor tissue was present in the sample and, therefore, is diagnostic of cancer in the subject. The invention also provides a method of determining the prognosis of a cancer patient.

20 Claims, 1 Drawing Sheet

FIG. 1

CANCER-ASSOCIATED MAR BINDING PROTEIN

This work was supported by grant RO1 CA39681-10 awarded by the National Institutes of Health. The United States Government has certain rights in this invention.

BACKGROUND OF THE INVENTION

1. Field of the Invention

This invention relates generally to the fields of molecular biology and medicine and more specifically to a protein that is active primarily in malignant tumor tissue but not in non-cancerous tissue, the protein activity being diagnostic of cancer in a subject.

2. Background Information

Cancer is the second most common cause of death in the United States. Breast cancer, for example, is diagnosed in more than 180,000 women in the United States each year. In most cases, the cancer is not detected until it becomes palpable. However, the prognosis is not good for a patient presenting with a palpable breast tumor. Due, in part, to the late detection of breast tumors, approximately one-third of the women diagnosed with breast cancer will die from the disease.

In order to detect breast cancer at an early stage, women that are 50 years of age or older and women that have a family history of breast cancer are encouraged to have yearly mammograms. Unfortunately, mammography cannot definitively confirm whether a breast tumor, particularly a small tumor, is malignant. Furthermore, mammography suffers from the limitation that it does not provide any information as to the type or stage of a breast cancer and cannot indicate whether an apparently benign tumor contains malignant tumor cells. Thus, mammography provides little if any prospective information as to the prognosis of a patient.

Currently, lymph node status provides the most reliable information as to the prognosis of a breast cancer patient. However, this method is not perfect, as about 20–30% of patients that have negative axillary lymph nodes will experience recurrence of the disease.

Significant research has been directed to identifying cancer-associated tumor markers. The recent association of breast cancer with the gene, brca-1 ("breast cancer-1"), was hailed as a break-through for identifying women at high risk of developing breast cancer. However, brca-1 is a very large gene that shows a significant degree of polymorphism in the human population. These characteristics of brca-1 will make the development of a screening assay much more complicated than initially hoped. In addition, brca-1 only is useful for identifying a subpopulation of breast cancers and likely will provide limited if any utility in predicting the prognosis of the disease.

Histologic examination of a biopsy sample of the tumor can provide more definitive information as to the type and stage of a tumor and, therefore, as to the prognosis of the patient. However, histologic examination suffers from the subjective nature of the method. Thus, a need exists to identify a cancer-associated tumor marker that is diagnostic of cancer and prognostic as to the course of the disease. The present invention satisfies this need and provides related advantages as well.

SUMMARY OF THE INVENTION

The present invention provides a nuclear matrix attachment region (MAR) DNA binding protein having an apparent molecular mass of about 114 kiloDaltons (kDa). The p114 MAR binding protein (p114-MBP) is characterized, in part, by having MAR binding activity in malignant tumor tissue such as breast cancer or lung cancer tissue but not in non-cancerous tissue, including, for example, normal breast tissue, benign breast tumors and normal lung tissue. Thus, the invention provides a cancer-associated MAR binding protein. In addition, the present invention provides an antibody that specifically binds p114-MBP.

The invention also provides methods of detecting the presence of malignant tumor tissue in a cell sample suspected of containing malignant tumor tissue and of diagnosing cancer in a subject. Malignant tumor tissue can be detected, for example, by contacting a cell sample with a MAR under conditions that allow the specific association of the MAR DNA sequence context with p114-MBP and detecting such specific association, which indicates the presence of p114-MBP MAR binding activity and, therefore, of malignant tumor tissue in the cell sample. Where the cell sample is obtained, for example, by biopsy from subject suspected of having cancer, the detection of p114-MBP activity in the sample is diagnostic of cancer in the subject.

The present invention further provides a method of determining the prognosis of a subject diagnosed as having cancer by determining the amount of p114-MBP MAR binding activity in the malignant tumor tissue. Such a prognosis can be made because the amount of p114-MBP activity detected is correlated to the tumor grade of the cancer.

DETAILED DESCRIPTION OF THE INVENTION

The present invention provides a nuclear matrix attachment region DNA binding protein that has an apparent molecular mass of about 114 kiloDaltons (kDa) and specifically associates with a nuclear matrix attachment region DNA sequence context (MAR). As used herein, the term "MAR" or "matrix attachment region DNA sequence context" means a region of DNA that binds chromatin to the nuclear matrix and consists of a cluster of at least two double stranded DNA sequences, called "ATC sequences," that unwind when subjected to superhelical stress. As used herein, the term "ATC sequence" means a DNA sequence that is about ten to about forty nucleotides in length, is greater than about 60% AT-rich and contains in one strand, in addition to adenine and thymine, either only cytosine or only guanine.

A MAR is referred to as a DNA sequence context because it cannot be defined by a traditional consensus-type nucleotide sequence. Instead, a MAR is defined by the combination of structural features, as described above, and the functional feature of unwinding when subjected to superhelical stress.

Naturally-occurring MARs from different species were identified by employing an unpaired DNA-specific probe, chloroacetaldehyde (CAA), to detect sequence contexts having the strong potential for extensive unwinding when subjected to superhelical strain (Kohwi-Shigematsu et al., *Proc. Natl. Acad. Sci., USA* 80:4389–4393 (1983); Kohwi-Shigematsu and Kohwi, *Cell* 43:199–206 (1985); Kohwi-Shigematsu and Kohwi, *Biochemistry* 29:9551–9560 (1990), each of which is incorporated herein by reference). This unwinding property of a MAR allows for binding of the MAR to the nuclear matrix, binding of a MAR binding protein to the MAR and augmentation of gene expression (Bode et al., *Science* 195–197 (1992), which is incorporated herein by reference).

Two MARs, for example, flank the immunoglobulin heavy chain (IgH) gene enhancer, which is continuously unpaired over a distance of more than 200 base pairs (bp) in supercoiled plasmid DNA (Cockerill et al., *J. Biol. Chem.* 262:5394–5397 (1987)). A short sequence motif, ATATAT, located in the MAR present in the 3'-region of the IgH enhancer is a nucleation site for unwinding, as point mutations substituting three bases in the ATATAT sequence completely abolished the unwinding property of the MAR.

A synthetic concatemerized, double-stranded 25 base pair oligonucleotide containing the unwinding core sequence of the 3' region of the IgH enhancer MAR has the properties of a naturally-occurring MAR (see Example I). This synthetic MAR unwinds under superhelical strain, binds strongly to the nuclear matrix with an affinity comparable to that observed with the 2 kilobase (kb) MAR present in the human β-interferon gene and enhances transcription of a linked reporter gene in stable transformants (Mielke et al., *Biochemistry* 29:7475–7485 1990, which is incorporated herein by reference; Kohwi-Shigematsu and Kohwi, supra, 1990; Bode et al., supra, 1992). In contrast, a similarly concatemerized, double-stranded oligonucleotide containing a mutated core sequence (see Example I) did not unwind when subjected to superhelical stress, had reduced binding affinity to the nuclear matrix and did not enhance gene transcription.

The identification of proteins that specifically recognize and bind a MAR can provide a means to alter gene expression at the chromatin level. Nucleolin, for example, which is present in most cell types, has been identified as a MAR binding protein (Dickinson and Kohwi-Shigematsu, *Mol. Cell. Biol.* 15:456–465 (1995), which is incorporated herein by reference). Topoisomerase II is another example of a MAR binding protein that is expressed in most cell types. These MAR binding proteins are considered to be structural components of the nuclear matrix involved in the higher order organization of chromatin structure. SAF-A (Romig et al, *EMBO J.* 11:3431–3440 (1992)), which also is known as hnRNP-U (Fackelmayer, *Eur. J. Biochem.* 221:749–757 (1994), is another MAR binding protein.

SATB1 also is a MAR binding protein (Dickinson et al., *Cell* 70:631–645 (1992), which is incorporated herein by reference). SATB1 has a deduced molecular weight of 85.9 kDa and migrates with an apparent molecular mass of 103 kDa as determined by SDS-PAGE. SATB1 binds to a MAR with a dissociation constant ($K_d$) of about $1 \times 10^{-9}$ to $1 \times 10^{-10}$ $M^1$. In contrast to previously described MAR binding proteins, SATB1 is predominantly expressed in immature thymocytes and is the first example of a tissue-specific MAR binding protein. As a result of its tissue-specific expression, SATB1 can be useful as a marker to identify the presence of immature T cells in the circulation as can occur, for example, in a subject having a T cell leukemia.

The present invention provides a MAR binding protein (p114-MBP) that is active primarily in malignant tumor tissues but not in non-cancerous tissues. Thus, the invention provides a cancer-associated MAR binding protein, p114-MBP, which can be used as a marker to distinguish malignant tumor tissue from non-cancerous tissue. In addition, the level of p114-MBP MAR binding activity is correlated to the stage of the cancer. For example, malignant breast tumor tissue obtained from a subject having an infiltrating ductal carcinoma with extensive metastases had a higher level of p114-MBP activity than breast cancer cells obtained from a subject having a mostly intraductal carcinoma. Thus, the amount of p114-MBP MAR binding activity in a tumor tissue can provide information as to the patient's prognosis, which is correlated to the tumor grade.

As disclosed herein, p114-MBP MAR binding activity was detected in malignant breast tumor tissue, but not in normal breast tissue including normal quiescent breast tissue cells or non-proliferating or proliferating benign breast tumor cells. Similarly, p114-MBP activity was detected in malignant lung tumor tissue, including large cell carcinoma, adenocarcinoma and squamous cell carcinoma, but not in normal lung tissue. In addition, p114-MBP activity was detected in two colorectal tumor cell lines, SO cells and H6 cells (Parsons et al., *Cell* 75:1227–1236 (1993), which is incorporated herein by reference) and can be present in various other cancers, including, for example, hepatocarcinoma, ovarian carcinoma and prostate cancer.

As used herein, the term "MAR binding activity" or "activity" when used in reference to p114-MBP means that p114-MBP can specifically associate with a MAR. Methods for identifying specific p114-MBP MAR binding activity include, for example, a gel shift assay and south-western blot analysis. MAR binding activity also can be identified using methods of affinity chromatography. As disclosed herein, p114-MBP activity was detected in malignant breast tumor tissue but not in normal breast tissue or benign breast tumor tissues and in malignant lung tumor tissue but not in normal lung tissue.

The MAR binding activity of p114-MBP was identified by a gel shift assay and by south-western blot analysis and p114-MBP was substantially purified by MAR affinity column chromatography (see Example I). When used in reference to p114-MBP, the term "substantially purified" means that the p114-MBP protein is in a form that is relatively free from contaminating lipids, proteins, nucleic acids or other cellular material normally associated with a protein in a cell. Substantially purified p114-MBP can be obtained using the methods described herein or otherwise known in the art, including, for example, by expressing a nucleic acid sequence encoding p114-MBP or by chemical synthesis. Using the methods disclosed herein, p114-MBP was obtained in a substantially purified form as determined by its migration as a single band following SDS-PAGE and silver staining.

p114-MBP was identified by its ability to specifically associate with a wild type but not a mutant MAR. For the experiments described herein, a synthetic wild type MAR, consisting of concatemers of the 25 bp ATC sequence shown below as SEQ ID NOS: 1 and 2, were synthesized. For affinity chromatography, random concatemers containing three or more repeats of the ATC sequence were used ($25_n$). For south-western blot analysis and gel shift assays, concatemers containing 5 ($25_5$) or 7 ($25_7$) repeats of the ATC sequence were used, although other multimers also can be used. These multimers, which are referred to wild type MAR probes, unwind when subjected to superhelical stress.

In addition, a mutant MAR, consisting of concatemers of the 24 bp ATC-like sequence shown as SEQ ID NOS: 3 and 4, were synthesized (see Example I; see, also, Bode et al., supra, 1992). For affinity chromatography, random multimers containing three or more repeats of the ATC-like sequence were used ($24_n$). For south-western blot analysis and gel shift assays, multimers containing 8 repeats of the ATC-like sequence were used ($24_8$), although other multimers also can be used. These multimers are referred to mutant MAR probes. Whereas the wild type MAR probe unwinds when subjected to superhelical stress, the mutant MAR probe, although AT-rich, does not unwind when subjected to superhelical stress.

p114-MBP specifically associates with a MAR such as a wild type MAR probe described above. When used in reference to p114-MBP and a MAR, the term "specifically associates" means that p114-MBP binds to the MAR with a dissociation constant of greater than about $5 \times 10^{-8}$M. The dissociation constant for p114-MBP and a MAR can be determined as disclosed in Example I. In addition, the specific association was demonstrated by showing that p114-MBP can be eluted from a mutant MAR affinity column using 0.1M KCl, whereas 0.4–0.6M KCl is required to elute p114-MBP from a wild type MAR affinity column. These results demonstrate that p114-MBP is not a non-specific AT-rich DNA binding protein.

p114-MBP binding activity was initially identified by south-western blot analysis of cellular extracts prepared from infiltrating ductal carcinoma cells obtained from a breast cancer patient and from SK-BR-3 cells (ATCC HTB 30), which is a poorly differentiated human breast adenocarcinoma cell line. p114-MBP bound the wild type MAR probe but not the mutant MAR probe. p114-MBP was substantially purified by fractionating the cell extracts first on a DNA affinity column containing the mutant MAR probe, to remove non-specific AT-rich DNA binding proteins, then on a DNA affinity column containing the wild type MAR probe (see Example I). p114-MBP migrated as a single band as determined by SDS-PAGE and silver staining and was not immunoreactive with antibodies specific for several known nuclear matrix proteins, including, for example, SATB1, SAF-A/hnRNP-U and nucleolin.

The present invention also provides active fragments of p114-MBP. When used in reference to p114-MBP, the term "active fragment" means an amino acid sequence that is a portion of the entire p114-MBP protein, provided the amino acid sequence retains the ability to specifically associate with a MAR. An active fragment of p114-MBP can be obtained, for example, by partial proteolysis of the substantially purified p114-MBP, by chemical synthesis of a portion of the amino acid sequence of p114-MBP or by expression of a nucleic acid sequence encoding a portion of p114-MBP. In view of the methods disclosed herein or otherwise known in the art, active fragments of p114-MBP readily can be identified.

A nucleic acid molecule encoding p114-MBP can be isolated using various methods well known in the art. For example, a cDNA encoding p114-MBP or an active fragment thereof can be identified by screening a cDNA library prepared from a malignant tumor tissue such as breast cancer or lung cancer tissue with the wild type MAR probe described above or with an anti-p114-MBP antibody. Methods for screening such a library were used, for example, to isolate a cDNA molecule encoding SATB1 (see Dickinson et al., supra, 1992). A nucleic acid molecule encoding p114-MBP can be obtained by determining a partial amino acid sequence of p114-MBP and preparing oligonucleotide probes that can be used to screen a breast cancer cell-derived cDNA library (see, for example, Sambrook et al., *Molecular Cloning: A laboratory manual* (Cold Spring Harbor Laboratory Press 1989); Paddock, *Meth. Enzymol.* 217:340–346 (Academic Press 1993), each of which is incorporated herein by reference). Thus, the present invention provides a nucleic acid molecule encoding p114-MBP.

The present invention also provides antibodies that specifically bind one or more epitopes of p114-MBP. As used herein, the term "antibody" is used in its broadest sense to include polyclonal and monoclonal antibodies, as well as polypeptide fragments of antibodies that retain a specific binding activity of at least about $1 \times 10^5$ M$^{-1}$ for an epitope of p114-MBP. In view of this definition, one skilled in the art would know that anti-p114-MBP antibody fragments such as Fab, F(ab')$_2$ and Fv fragments can retain specific binding activity for p114-MBP and, thus, are included within the definition of an antibody.

The term "antibody" as used herein includes naturally occurring antibodies as well as non-naturally occurring antibodies and fragments thereof that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

Particularly useful non-naturally occurring antibodies include chimeric antibodies and humanized antibodies. As used herein, the term "chimeric antibody" means an antibody having a human constant region and a variable region from an organism other than a human. For example, a chimeric antibody useful in the invention can consist of a human IgG constant region and a variable region obtained from a mouse anti-human p114-MBP antibody. As used herein, the term "humanized antibody" means an antibody having human constant and framework regions and hypervariable regions from an organism other than a human. For example, a humanized antibody useful in the invention can consist of the amino acids that form the hypervariable region of a mouse anti-human p114-MBP antibody and the amino acids that form the framework region and constant regions of a human IgG class antibody. Chimeric antibodies and humanized antibodies are particularly useful for administration to a human subject, since the likelihood of an immune response by the subject against the antibody is minimized.

Anti-p114-MBP antibodies can be prepared using substantially purified p114-MBP or a p114-MBP fusion protein as an immunogen. In addition, a peptide fragment of p114-MBP can be used as an immunogen. Methods for raising an antibody are routine and described, for example, by Harlow and Lane, *Antibodies: A laboratory manual* (Cold Spring Harbor Laboratory Press, 1988), which is incorporated herein by reference. A form of p114-MBP useful as an immunogen can be prepared from natural sources, as described herein, produced recombinantly or chemically synthesized.

In some cases, a protein such as p114-MBP may be poorly immunogenic due, for example, to a high degree of conservation of the protein among various species. In addition, a fragment of p114-MBP may not be immunogenic. However, a non-immunogenic protein or fragment thereof can be made immunogenic by coupling it to a carrier molecule such bovine serum albumin or keyhole limpet hemocyanin. Various other carrier molecules and methods for coupling a hapten to a carrier molecule are well known in the art (see, for example, Harlow and Lane, supra, 1988).

Polyclonal anti-p114-MBP antibodies can be raised, for example, in goats, rabbits or mice. In addition, monoclonal antibodies can be obtained using known methods (Harlow and Lane, supra, 1988). Essentially, spleen cells from a p114-MBP-immunized animal can be fused to an appropriate myeloma cell line such as SP/02 or P3×653.Ag8 myeloma cells to produce hybridoma cells. Cloned hybridoma cell lines can be screened using labelled p114-MBP polypeptide to identify clones that secrete anti-p114-MBP monoclonal antibodies. Methods for labelling a polypeptide are well known (see below).

Hybridomas that express antibodies having a desirable specificity and affinity can be isolated and utilized as a continuous source of monoclonal anti-p114-MBP antibodies, which can be useful for preparing a kit containing an anti-p114-MBP antibody. Methods for identifying an anti-p114-MBP antibody having an appropriate specificity and affinity and, therefore, useful in the invention also are known in the art and include, for example, enzyme-linked immunosorbent assays, radioimmunoassays and precipitin assays (Harlow and Lane, supra, 1988; chap. 14).

An anti-p114-MBP antibody of the invention can be useful, for example, to purify p114-MBP from a sample. For example, anti-p114-MBP antibodies can be attached to a solid substrate such as a resin and can be used to affinity purify p114-MBP. An anti-p114-MBP antibody also can be used to identify the presence of p114-MBP in a sample. In this case, the anti-p114-MBP antibody can be labelled so as to be detectable. An anti-p114-MBP antibody can be detectably labelled using methods well known in the art (see, for example, Harlow and Lane, 1988; chap. 9). For example, an antibody can be labelled with any of various detectable moieties including a radiolabel, an enzyme, biotin or a fluorochrome. Following contact of a labelled antibody with a sample such as a tissue homogenate or a histological section of a tissue, specifically bound labelled antibody can be identified by detecting the particular moiety.

A labelled second antibody also can be used to identify specific binding of an unlabelled anti-p114-MBP antibody. A second antibody generally will be specific for the particular class of the first antibody. For example, if an anti-p114-MBP antibody is of the IgG class, a second antibody will be an anti-IgG antibody. Such second antibodies are readily available from commercial sources. The second antibody can be labelled using a detectable moiety as described above. When a sample is labelled using a second antibody, the sample is first contacted with a first antibody, then the sample is contacted with the labelled second antibody, which specifically binds to the first antibody and results in a labelled sample.

The invention also provides a method of detecting the presence of tumor tissue in a cell sample. The presence of the tumor tissue is identified by detecting the presence of p114-MBP MAR binding activity in the cell sample. As used herein, the term "cell sample" is used in its broadest sense to include, for example, whole cells, a tissue sample such as a biopsy obtained from a subject, a crude cell homogenate or a cell extract. Thus, a cell sample can be used directly, for example, for histologic analysis or the cell sample can be further processed such that cellular proteins present in the cell sample can be manipulated. It should be recognized that, since the sample is to be assayed for the presence of p114-MBP MAR binding activity, the sample should be handled such that the likelihood of proteolysis is minimized.

The claimed method of detection depends on identifying p114-MBP MAR binding activity, which is detectable in various malignant tumor tissues including, for example, malignant breast tumor tissue and malignant lung tumor tissue but not in normal breast tissue, benign breast tumors or normal lung tissue. Methods for detecting the MAR binding activity of a DNA binding protein such as p114-MBP in a sample are well known in the art and include, for example, DNA binding assays such as a gel shift assay or a south-western blot analysis.

An immunoassay using an antibody that specifically binds to p114-MBP can be used to detect the presence of p114-MBP in a sample. It should be recognized, however, that the amount of p114-MBP expressed in a tissue need not necessarily correlate with the level of p114-MBP MAR binding activity in the tissue. For example, the p114-MBP binding activity present in a tumor tissue can be due to activation of p114-MBP that is normally present in the tissue. It is further recognized, however, that an anti-p114-MBP antibody can be obtained that can distinguish between a form of p114-MBP than can bind a MAR and a form that does not bind a MAR.

As disclosed herein, p114-MBP MAR binding activity was detected in breast tumor tissue, lung tumor tissue and in two colorectal tumor cell lines using gel shift assays and south-western blot analysis, both of which demonstrated the specific association of the wild type MAR probe with the protein. For south-western blot analysis, cell extracts were prepared and proteins in the extract were size-fractionated by electrophoresis. The proteins then were transferred to a filter and incubated with the wild type MAR probe, which was detectably labelled. Methods for detectably labelling a nucleic acid sequence such as a MAR probe are well known in the art, as are detectable labels, including, for example, radionuclides, fluorochromes and biotin. Binding of the wild type MAR probe to a protein having an apparent molecular mass of 114 kDa, i.e., p114-MBP, was detected in samples known to contain, for example, malignant breast tumor tissue and malignant lung tumor tissue but not in samples of normal breast tissue, benign breast tumors or normal lung.

South-western blot analysis was performed on various breast tissue samples, including five infiltrating ductal carcinomas and their adjacent normal tissues, two normal breast tissue samples from healthy individuals (see FIG. 1), and several benign tumors, including fibroadenoma, proliferative fibrocystic change, fibrocystic change, atypical ductal hyperplasia and atypical lobular hyperplasia (reviewed by Schnitt and Connolly, in *Pathology of Benign Breast Disorders. Breast diseases.* 2nd ed., pages 13–15 (J. B. Lippincott Co. 1993)). In addition, various breast tumor cell lines and normal human epithelial MCF-10 (ATCC CRL 10317) cells were examined.

A band representing p114-MBP was observed only in the malignant breast cancer samples and in the breast cancer cell lines. No p114-MBP activity was present in normal breast tissue, including apparently normal breast tissue that was resected from regions adjacent to five infiltrating ductal carcinomas (see FIG. 1), in the various benign tumors or in the MCF-10 cells. Thus, the claimed method provides a means of selectively detecting the presence of malignant breast tumor tissue in a cell sample. Similarly, various lung tumor tissue samples, including large cell carcinoma, adenocarcinoma and squamous cell carcinoma, contained p114-MBP binding activity, whereas no such activity was detected in normal lung tissue samples.

The present invention provides a method of diagnosing cancer in a subject suspected of having cancer. The claimed method depends on detecting the presence of p114-MBP activity in a cell sample obtained, for example, by needle biopsy or surgical resection from the subject. The cell sample can be contacted with a MAR under conditions that allow the specific association of the MAR with p114-MBP. Specific association of the MAR and p114-MBP indicates that malignant tumor tissue was present in the cell sample and, therefore, is diagnostic of cancer in the subject. The disclosed method is particularly useful because, if p114-MBP activity is detected, the level of p114-MBP activity can indicate the tumor grade and, therefore, can be of prognostic value to the oncologist.

A cell sample also can be contacted with an anti-p114-MBP antibody, where specific binding of the antibody indicates the presence of p114-MBP in the cell sample. For example, immunohistologic analysis of a biopsy sample readily can be performed in a hospital pathology laboratory. Where the antibody can detect p114-MBP that can bind a MAR, such a method provides for the rapid analysis of a suspected cancer while the patient remains under anesthesia and, if cancer is detected, the tumor can be resected.

In view of the clinical significance of the disclosed method for diagnosing cancer in a subject, it can be desirable to provide a kit useful for this purpose. Such a kit can contain, for example, an oligonucleotide probe representing a MAR, which, if desired, can be attached to a solid support and can be detectably labelled, for example, with a fluorochrome. The kit also can contain, if desired, standard reagents such as buffers that provide suitable conditions for performing a particular assay and predetermined amounts of p114-MBP, which can provide a means to standardize the assay and more readily determine whether a cell sample obtained from a subject contains substantial p114-MBP activity.

As used herein, the term "substantial p114-MBP activity" means that p114-MBP binding to a MAR can readily be detected using, for example, a gel shift assay or a southwestern blot analysis. It is recognized that the level of detection of p114-MBP activity depends on the sensitivity of the assay being used. For example, using the gel shift assay or south-western blot analysis as disclosed herein, substantial p114-MBP binding activity is not detected in non-cancerous tissue. It is recognized, however, that a more sensitive method of detection may reveal that presence of p114-MBP activity in non-cancerous tissue, albeit at very low levels as compared to the level in a corresponding tumor tissue. In such a case, the skilled artisan would know that a population of cell samples obtained from healthy individuals must be analyzed in order to determine the "normal" level of p114-MBP activity in various non-cancerous tissues. Having determined a range of normal p114-MBP activity present in non-cancerous tissue, a statistically significant increased level of p114-MBP MAR binding activity can be determined and can be diagnostic of cancer. Such a statistically significant increased level of p114-MBP MAR binding activity above a known normal level of activity is considered to be substantial p114-MBP activity as defined herein.

The present invention is particularly advantageous in that not only can a diagnosis of cancer be made but, in addition, a prognosis can be made for a subject diagnosed as having cancer. Specifically, the amount of p114-MBP activity present, for example, in malignant breast tumor tissue is indicative of the tumor grade of the cancer. For example, south-western blot analysis was performed on thirty-nine breast cancer samples of varying tumor type, clinical stage and tumor grade. All thirty-nine samples were positive for p114-MBP MAR binding activity. The bands representing p114-MBP were quantitated by laser densitometry and the density of each band, which is a measure of the amount of p114-MBP MAR binding activity, was compared with the clinical stage, lymph node status and tumor grade of the corresponding tumor. The amount of p114-MBP activity correlated with the tumor grade, which is a measure of the differentiation state of the tumor cells. In particular, the amount of p114-MBP activity was greater in poorly differentiated infiltrating ductal carcinoma as compared to moderately differentiated and well-differentiated infiltrating ductal carcinoma, including tumors that are predominantly intraductal. These results were confirmed using gel shift assays, in which p114-MBP binding activity increased with increasing tumor grade.

The following examples are intended to illustrate but not limit the present invention.

EXAMPLE I

Purification and Characterization of p114-MBP

This example describes the method used to substantially purify and characterize the 114 kDa matrix associated region DNA sequence context binding protein, p114-MBP, from malignant breast tumor tissue and from a breast cancer cell line.

A. Cell extract preparation

Human SK-BR-3 (ATCC HTB 30) breast adenocarcinoma cells were grown in a Cell Factory™ (Nunc; Roskilde Denmark) at 37° C. (5% $CO_2$) in McCoy's 5a medium (Irvine Scientific; Irvine Calif.) supplemented with 10% heat-inactivated fetal bovine serum, 2 mM glutamine, 100 U/ml penicillin and 100 mg/ml streptomycin. Cells were resuspended by repeated pipetting in growth medium, then collected by centrifugation for 5 min at 2,500 rpm in a Beckman TJ-6 centrifuge and washed 1x with cold phosphate-buffered saline (PBS).

In some experiments, whole breast cancer tissue obtained by surgical resection was used to purify p114-MBP or to characterize the expression of p114-MBP. All breast cancer tissue samples were obtained by surgery prior to chemotherapy. Normal breast tissue, benign breast tumor tissue and malignant breast cancer tissue samples were obtained from the breast tumor surgical team, Tochigi Cancer Center, Japan; Human Tissue Bank of the University of California, San Diego; and Cooperative Human Tissue Network, Western Division, Case Western Reserve University. Pathological data, including TNM staging, lymph node status and tumor grade, were provided for each cancer tissue. The tissues were immediately frozen following surgical resection and maintained at −80° C. For p114-MBP purification, 1 g tissue was removed and treated as described below.

The cell pellet obtained from a 500 ml cell suspension culture or from the breast tissue sample was resuspended in 10 ml extraction buffer (0.4M KCl, 10 mM sodium phosphate buffer, pH 7.4, 10% glycerol, 0.5 mM dithiothreitol (DTT), 0.1 mM phenylmethylsulfonylfluoride (PMSF), 10 µg/ml leupeptin and 10 µg/ml aprotinin). Cells were lysed in a Dounce homogenizer (50 strokes, pestle A) and the extract was centrifuged at 38,000 rpm for 1 hr in a T865.1 rotor in a Sorvall centrifuge. The supernatant (crude cell extract) was assayed by the gel shift assay or south-western blot analysis for binding activity or was used to purify p114-MBP by MAR affinity chromatography.

The protein concentrations of whole cell extracts were determined using a protein assay kit (Bio-Rad; Hercules Calif.). The concentrations of purified proteins were determined using the Quantigold™ assay reagent (Diversified Biotech). Proteins were separated by 7.5% SDS-PAGE (Laemmli, *Nature* 227:680–685 (1970), which is incorporated herein by reference) and visualized by silver staining. Equivalent volumes for each fractionation step were subjected to SDS-PAGE using a 7.5% gel.

B. MAR affinity chromatography p114-MBP was obtained in a substantially purified form by fractionating crude cell extract prepared from infiltrating ductal carcinoma tissue on a MAR affinity chromatography column. DNA affinity chromatography was performed using a modification of the method of Kadonaga and Tjian (*Proc. Natl. Acad. Sci. USA* 83:5889–5893 (1986), which is incorporated herein by reference).

Wild type and mutant MAR double stranded oligonucleotides were synthesized. The wild type MAR was prepared by annealing the complementary ATC sequences: 5'-TCTTTAATTTCTAATATATTTAGAAttc-3' (SEQ ID NO: 1) and 5'-TTCTAAATATATTAGAAATTAAAGAgaa-3' (SEQ ID NO: 2; lowercase indicates single-strand overhangs), then concatemerizing the ATC sequence. The mutant MAR was prepared by annealing the complementary ATC-like sequences: 5'-TCTTTAATTTCTACTGCT TTAGAA-3' (SEQ ID NO: 3) and 5'-TTCTAAAGCAGTAGAAATTAAAGA-3' (SEQ ID NO: 4), which contain 3 base changes and one base deletion as compared to the ATC sequences used to construct the wild type MAR probe, then concatemerizing the ATC-like sequence.

The double stranded oligomer ATC sequences (25 nucleotides) or ATC-like sequences (24 nucleotides) were phosphorylated at their 5'-ends and ligated to form concatemers having varying numbers of repeats. Concatemers consisting of trimers or greater were collected as a mixture ($25_n$ or $24_n$). Approximately 200 µg of each mixture of oligomers was coupled to 1 ml cyanogen bromide-activated Sepharose 6MB™ (Pharmacia; Uppsala Sweden), then the affinity matrices were washed extensively with buffer Z (25 mM Hepes ($K^+$), pH 7.8, 12.5 mM $MgCl_2$, 1 mM DTT, 20% glycerol (vol:vol), 0.1% Nonidet P-40™ (vol:vol)) and loaded into mini-columns to obtain a wild type MAR ($25_n$) column and mutant MAR ($24_n$) column.

Prior to adding the breast cell extract to the column, 5 ml of the crude cell extract in the extraction buffer described above was incubated with 50 µg double stranded poly (dI-dC)/poly (dI-dC) and 100 µg denatured salmon sperm DNA for 10 min on ice, then centrifuged at 10,000 rpm in a Sorvall SS34 rotor and diluted 4x with buffer Z. The diluted extract was loaded onto a column containing the mutant MAR probe (1 ml bed vol) at a rate of 15 ml/hr and washed with 15 ml buffer Z containing 0.1M KCl.

The flow through fraction from the mutant MAR column was collected and loaded onto a column containing the wild type MAR probe (1 ml bed vol) at a rate of 15 ml/hr and washed with 2×15 ml buffer Z containing 0.1M KCl. The bound proteins were eluted sequentially with 2 ml buffer Z containing 0.2, 0.4, 0.6, 0.8 and 1.0M KCl; 0.5 ml fractions were collected. Fractions containing the p114-MBP MAR binding activity eluted in the 0.4–0.6M KCl fractions and were concentrated by centrifugation in Centriprep-50™ micro-concentrators (Amicon; Beverly Mass.). The samples were desalted by dilution with PBS and centrifugation in Centriprep-50™ units.

C. Gel shift assay p114-MBP binding activity was determined using the gel shift assay. The mobility of p114-MBP/MAR complexes in non-denaturing gels was determined using the method described by Dickinson et al., supra, 1992.

A double stranded wild type MAR probe, which was a concatemer consisting of 5 repeats of the ATC sequence ($25_5$) shown as SEQ ID NOS: 1 and 2, and mutant MAR probe, which was a concatemer consisting of 8 repeats of the ATC-like sequence ($24_8$) shown as SEQ ID NOS: 3 and 4, were end-labeled at both ends with the Klenow fragment of DNA polymerase (see Sambrook et al., supra, 1989). Binding reactions were performed using 0.5 ng labelled MAR probe and varying amounts of cell extract or affinity-purified protein in a total volume of 20 µl. In some experiments, 100 ng unlabelled wild type or mutant MAR probe was added as a competitor to determine the specificity of p114-MBP binding activity.

Following binding, the samples were separated by electrophoresis in a 6% polyacrylamide mini-gel containing 0.05% bisacrylamide, 5% glycerol and 0.5x Tris-borate-EDTA (Sambrook et al., supra, 1989). In some experiments, bound and free labelled MAR probe was quantitated by laser densitometry of short exposure autoradiographs of the dried gels.

p114-MBP substantially bound the wild type MAR probe but not the mutant MAR probe. Specificity of binding of p114-MBP to the wild type MAR probe was confirmed by showing that binding to the probe was competed away when reactions were performed in the presence of unlabelled wild type MAR but not by the same amount of mutant MAR. These results demonstrate that p114-MBP specifically associates with a MAR.

The dissociation constant ($K_d$) of p114-MBP and the wild type MAR probe was determined. Binding reactions were performed in protein excess using 40 pM labelled wild type MAR probe and increasing protein concentrations. The $K_d$ was estimated from the protein concentration required for a 50% shift of the probe (Fried and Crothers, *Nucl. Acids Res.* 9:6505–6525 (1981); Koudelka et al., *Nature* 326:886–888 (1987), each of which is incorporated herein by reference). Under the reaction conditions for these experiments using the synthetic wild type MAR probe, p114-MBP bound to the MAR with a $K_d$ of about $1\times10^{-9}$M. These results demonstrate that p114-MBP binds with high affinity to a MAR.

D. South-western blot analysis

Twenty µg of crude cell extract prepared from either cultured cells or from breast tissue as described above was mixed in SDS loading buffer and heated at 68° C. for 1 min. The proteins were separated by SDS-PAGE on a 7.5% gel, then were electroblotted onto Immobilon P™ (Millipore; Bedford Mass.) membrane using sodium phosphate (pH 6.8) blotting buffer (50 V limit, 1 mA; 1 hr).

Blots were blocked in TST (20 mM Tris-HCl, pH 7.4, 0.5M NaCl, 0.05% Tween 20) containing 4% BSA, then washed in binding buffer (20 mM Tris-HCl, pH 7.4, 50 mM NaCl, 1 mM DTT, 0.25% BSA, 5 mM $MgCl_2$) for 1 hr. Salmon sperm DNA was added to 40 µg/20 ml and poly(dI-dC) was added to 100 µg/20 ml, then the blot was incubated for 30 min at RT. Radiolabelled wild type MAR probe ($25_5$) was added and blots were incubated 30 min at RT, then washed 4x with binding buffer for 10 min each and exposed to X-ray film. The results of these assays confirmed that the wild type MAR probe specifically associated p114-MBP.

E. Western blot analysis

Anti-SATB1 polyclonal antibodies were prepared as described by Dickinson et al., supra, 1992. Anti-nucleolin antibodies were prepared as described by Dickinson and Kohwi-Shigematsu, supra, 1995. Anti-tubulin antibodies were obtained from Sigma Immuno Chemicals (St. Louis Mo.).

Proteins were separated by 7.5% SDS-PAGE, then electrophoretically transferred to Immobilon P™ membranes in 20 mM $Na_2HPO_4/NaH_2PO_4$ buffer, pH 6.8. Biotinylated high molecular weight protein markers (Bio-Rad) were run as internal size standards. The filters were blocked with TST buffer (20 mM Tris-HCl, pH 7.4, 0.5M NaI, 0.05% Tween 20) containing 5% BSA, then washed with TST buffer.

The filters were incubated with rabbit anti-SATB1 serum (1:1000), then washed with TST and incubated simultaneously with 1:15,000 goat anti-rabbit antibody-conjugated horseradish peroxidase and avidin-labeled horseradish peroxidase (Bio-Rad). For detection of nucleolin, the blots were incubated with mouse anti-nucleolin serum (1:1000), then with 1:3,000 goat anti-mouse antibody-conjugated horseradish peroxidase. Following extensive washing in TST, the blots were incubated with ECL™ reagents (Amersham; Arlington Heights Ill.) and exposed to X-ray film for visualization of protein bands. p114-MBP did not react with anti-nucleolin or anti-SATB1 (or with anti-SAF-A/hnRNP-U antibodies), indicating that p114-MBP is antigenically distinct from these known MAR binding proteins.

EXAMPLE II p114-MBP MAR Binding Activity in Breast Cancer Cells

This example demonstrates that p114-MBP activity is present in breast cancer cells but not in normal breast cells or in benign breast tumor cells.

Figure 1:
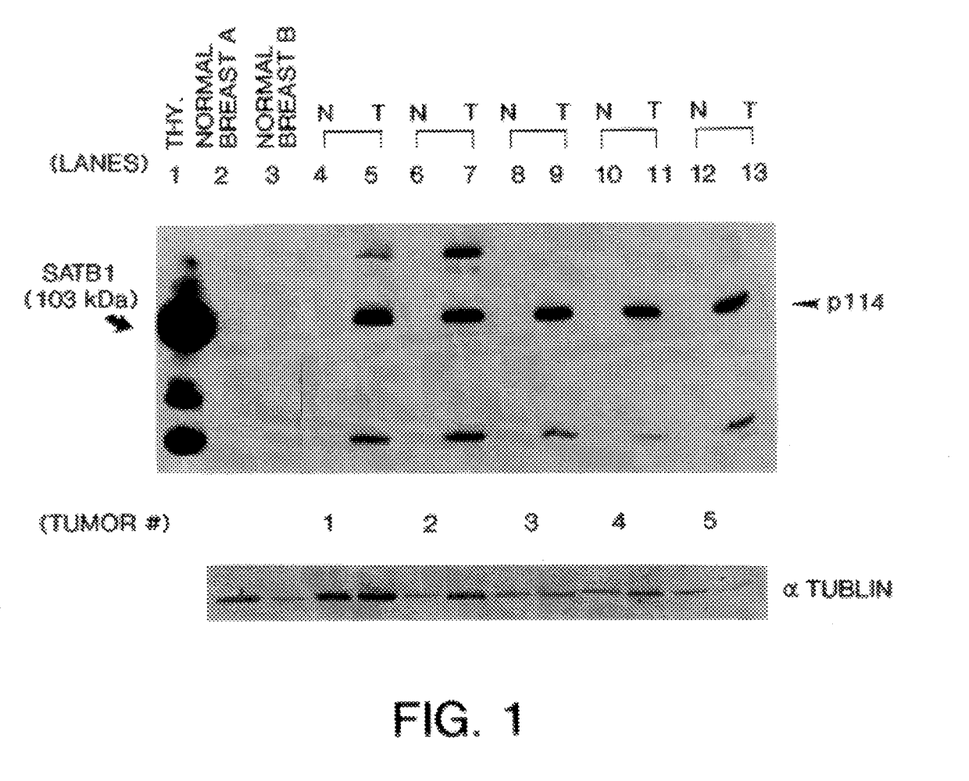
FIG. 1 shows that p114.-MBP activity is present in breast tumor tissue but not in normal breast tissue. Breast cancer tissue (lanes 5, 7, 9, 11 and 13; "T") and adjacent normal breast tissue (lanes 4, 6, 8, 10 and 12; "N") were examined from each of five different subjects as indicated (1-5; "tumor #"). Normal breast tissue from two healthy individuals also was examined (lanes 2 and 3). The migration of the 103 kDa SATB1 protein, which is expressed in thymus (lane 1; "Thy"), is shown for comparison. The migration position of p114-MBP is indicated ("p114"). α-tubulin is shown to indicate the relative amounts of protein loaded in each lane.

South-western blot analysis was performed using 20 μg cell extract protein of 5 different infiltrating ductal carcinoma samples, their adjacent normal tissues and two normal breast tissue samples from healthy individuals. As shown in FIG. 1, p114-MBP MAR binding activity was detected in the breast cancer samples, but not in the normal appearing breast tissue adjacent to the cancer or in normal breast tissue. These results demonstrate that p114-MBP activity is present in malignant breast tumor tissue but not normal breast tissue.

South-western blot analysis also was performed on cell extract proteins of benign breast tumors exhibiting fibroadenoma, fibrocystic changes, proliferative fibrocystic change, atypical ductal hyperplasia and atypical lobular hyperplasia. p114-MBP activity was not detected in any of these cell samples or in immortalized human epithelial MCF-10 cells or normal human fibroblasts (not shown).

Similarly, cellular protein extracts obtained from various malignant lung tumors, including large cell carcinoma, adenocarcinoma and squamous cell carcinoma, contained p114-MBP activity, whereas normal lung tissue exhibited no such activity. In addition, p114-MBP MAR binding activity was detected in two colorectal tumor cell lines (Parsons et al., supra, 1993).

Thirty-nine additional breast tumors of varying clinical stages and grades were examined for p114-MBP MAR binding activity by south-western blot analysis. In these experiments, the density of each band was quantitated by laser densitometry. When the various samples were grouped according to the differentiation state of the breast cancer and ranked within each group according to the amount of p114-MBP activity present in the sample, the amount of p114-MBP activity generally was higher, for example, in advanced tumors of mostly infiltrating ductal carcinoma from patients presenting with extensive metastases as compared with early stages of tumors that mostly represent intraductal carcinoma (not shown).

While a significant correlation was observed between p114-MBP binding activity and tumor grade, the binding activity did not necessarily correlate with the stage of the tumor. For example, a patient having an early stage cancer (stage 1) showed an intense band for p114-MBP. Remarkably, however, this patient suffered from metastasis three years after the initial surgery and died while other patients diagnosed as stage 0 and stage 1 and showing minimal p114-MBP activity remained cancer free during that period. Thus, p114-MBP band intensity as determined by south-western blot analysis can be useful for diagnosing patients with early stage disease that are candidates for aggressive treatment. Currently, no other prognostic indicators are available to identify those node-negative patients who will die from the disease and those who will remain free of the disease.

Although the invention has been described with reference to the disclosed examples, it should be understood that various modifications can be made without departing from the spirit of the invention. Accordingly, the invention is limited only by the following claims.

We claim:

1. A substantially purified protein, p114-MBP, having the following characteristics:
   a. an apparent molecular mass of about 114 kDa as determined by SDS-PAGE on a 7.5% gel; and which
   b. specifically associates with a matrix attachment region DNA sequence context (MAR) with a dissociation constant greater than about $5 \times 10^{-8}$ M,
wherein said p114-MBP is obtainable from a malignant tumor tissue and wherein said p114-MBP is not specifically bound by an antibody that specifically binds a protein selected from the group consisting of SATB1, nucleolin and SAF-A/hnRNP-U.

2. The protein of claim 1, wherein said protein is substantially purified from malignant breast tumor tissue.

3. The protein of claim 1, wherein said protein is substantially purified from malignant lung tumor tissue.

4. An antibody that specifically binds the protein of claim 1.

5. A method of detecting the presence of a malignant tumor tissue in a cell sample, comprising the steps of:
   a. contacting the cell sample with a MAR under conditions that allow the specific association of said MAR with p114-MBP; and
   b. detecting the specific association of said MAR with said p114-MBP, wherein said specific association indicates the presence of malignant tumor tissue in said cell sample.

6. The method of claim 5, wherein said malignant tumor tissue is malignant breast tumor tissue.

7. The method of claim 5, wherein said malignant tumor tissue is malignant lung tumor tissue.

8. The method of claim 5, wherein said MAR is attached to a solid substrate.

9. The method of claim 5, wherein said specific association is detected using a gel shift assay.

10. The method of claim 5, wherein said specific association is detected by south-western blot analysis.

11. A method of diagnosing cancer in a subject suspected of having cancer, comprising the steps of:
    a. obtaining a cell sample suspected of containing malignant tumor tissue from the subject;
    b. contacting said cell sample with a MAR DNA sequence context, under conditions that allow the specific association of said MAR DNA sequence context with p114-MBP; and
    c. detecting the specific association of said MAR DNA sequence context with said p114-MBP, wherein said specific association indicates the presence of malignant tumor tissue in said sample, which is diagnostic of cancer in said subject.

12. The method of claim 11, wherein said cancer is breast cancer.

13. The method of claim 11, wherein said cancer is lung cancer.

14. The method of claim 11, wherein said cell sample is a biopsy sample.

15. The method of claim 11, wherein said MAR is attached to a solid substrate.

16. The method of claim 11, wherein said specific association is detected using a gel shift assay.

17. The method of claim 11, wherein said specific association is detected by south-western blot analysis.

18. A method of determining the prognosis for a cancer patient, comprising the steps of:

a. obtaining a cell sample containing malignant tumor tissue from the patient; and b. determining the amount of p114-MBP binding activity in said cell sample, wherein the level of p114-MBP binding activity is correlated with the prognosis for said patient.

19. The method of claim 18, wherein said cancer is breast cancer.

20. The method of claim 18, wherein said cancer is lung cancer.

* * * * *

UNITED STATES PATENT AND TRADEMARK OFFICE
CERTIFICATE OF CORRECTION

PATENT NO. : 5,624,799
DATED : April 29, 1997
INVENTOR(S) : Kohwi-Shigematsu et al.

It is certified that error appears in the above-identified patent and that said Letters Patent is hereby corrected as shown below:

In column 2, line 33, please delete "p114.-MBP" and replace therefor with --p114-MBP--.

In column 4, line 3, please delete "tissues but:not in" and replace therefor with --tissues but not in--.

In column 4, line 66, please delete "referred to wild type" and replace therefor with --referred to as wild type--.

In column 5, lines 9 and 10, please delete "are referred to mutant" and replace therefor with --referred to as mutant--.

In column 6, line 65, please delete "molecule such bovine" and replace therefor with --molecule such as bovine--.

In column 13, line 6, please delete "0.5M Nal" and replace therefor with --0.5M NaCl--.

In column 14, line 13, please delete "band Was quantitated" and replace therefor with --band was quantitated--.

Signed and Sealed this

Sixteenth Day of June, 1998

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 28 base pairs
      ( B ) TYPE: nucleic acid
      ( C ) STRANDEDNESS: double
      ( D ) TOPOLOGY: linear    ( i i ) MOLECULE TYPE: DNA (genomic)

( x i ) SEQUENCE DESCRIPTION: SEQ ID NO:1:

TCTTTAATTT CTAATATATT TAGAATTC      28

( 2 ) INFORMATION FOR SEQ ID NO:2:

( i ) SEQUENCE CHARACTERISTICS:
    ( A ) LENGTH: 28 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:2:

TTCTAAATAT ATTAGAAATT AAAGAGAA                                    2 8

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

TCTTTAATTT CTACTGCTTT AGAA                                        2 4

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

TTCTAAAGCA GTAGAAATTA AAGA                                        2 4